United States Patent [19]

Girard et al.

[11] Patent Number: 5,688,914
[45] Date of Patent: Nov. 18, 1997

[54] COMPOSITION CONTAINING A B EPITOPE OF THE ENVELOPE GLYCOPROTEIN OF A RETROVIRUS AND A T EPITOPE OF ANOTHER DISTINCT PROTEIN OF THIS RETROVIRUS

[75] Inventors: Marc Girard; Jean-Claude Gluckman, both of Paris; El Mustapha Bahraoui, Marseille, all of France

[73] Assignees: Institut Pasteur; Universite Pierre et Marie Curie Paris VI, both of France

[21] Appl. No.: 150,249

[22] Filed: Nov. 9, 1993

Related U.S. Application Data

[63] Continuation of Ser. No. 939,576, Sep. 3, 1992, abandoned, which is a continuation of Ser. No. 821,880, Nov. 17, 1992, abandoned, which is a continuation of Ser. No. 659,422, filed as PCT/FR90/00620 Aug. 17, 1990 published as WO91/02544 Mar. 7, 1991, abandoned.

[30] Foreign Application Priority Data

Aug. 18, 1989 [FR] France ................... 89 110044

[51] Int. Cl.$^6$ ............... C07K 1/00; C07K 14/00; A61K 39/21; A61K 39/12
[52] U.S. Cl. ............ 530/350; 530/395; 424/188.1; 424/184.1; 424/208.1; 424/204.1
[58] Field of Search ............... 536/27; 530/350, 530/395; 424/89

[56] References Cited

U.S. PATENT DOCUMENTS 5,013,548  5/1991  Haynes et al. ............ 424/89
5,019,387  5/1991  Haynes et al. ............ 424/89

FOREIGN PATENT DOCUMENTS 0 328 390 A2  8/1989  European Pat. Off.

OTHER PUBLICATIONS

Bahraoui, et al, 1990, "Immunogenicity of the ..." AIDS Res. Human Retroviruses.
Chakrabarti, et al, 1987, "Sequence of simian immunodeficiency ..." Nature 328:543–547.
Goudsmit, et al, 1988, "Human immunodeficiency ..." PNAS, 85:4478–4482.
Palker, et al, 1989, J. Immunol. 142:3612–3619.
Guy, et al, 1987, Nature 330:266–269.
Culmann, et al, 1989, Eur. J. Immunol. 19:2383–2386.
Guy, et al, 1987, "HIV F/3'ORF encodes a phosphorylated GTP–binding ..." Nature 330:266–269.
Culmann, et al, 1989, "An antigenic peptide of the HIV–1 NEF Protein ..." Eur. J. Immunol. 19:2383–2386.

Shoeman et al., "Comparison of Recombinant Human Immunodeficiency Virus gag Precursor and gag/env Fusion Proteins and a Synthetic env Peptide as Diagnostic Regents", Analytical Biochemistry, 161:370–379 (1987).
Ho et al., "Second Conserved Domain of gp120 Is Important for HIV Infectivity and Antibody Neutralization", Science, 239:1021–1023 (1988).
Schrier et al., "B– and T–Lymphocyte Responses to an Immunodominant Epitope of Human Immunodeficiency Virus", Journal of Virology, 62:2531–2356 (1988).
Sternberg et al., "Prediction of Antigenic Determinants and Secondary Structures of the Major AIDS Virus Proteins", FEBS Letters, 218:231–237 (1987).
Zvelebil et al., "Predictions of Liner T–cell and B–cell Epitopes in Proteins Encoded by HIV–1, HIV–2 and SIV$_{MAC}$ and the Conservation of these Sites Between Strains", FEBS Letters, 242:9–21 (1988).
Putney et al., "HTLV–III/LAV–Neutralizing Antibodies to an E.coli–Produced Fragment of the Virus Envelope", Science, 234:1392–1395 (1986).
Palker et al., "Type–specific Neutralization of the Human Immunodeficiency Virus With Antibodies to env–encoded Synthetic Peptides", Proc. Natl. Acad. Sci. USA, 85:1932–1936 (1988).
Goudsmit et al. "Human Immunodeficiency Virus Type 1 Neutralization Epitope With Conserved Architecture Elicits Early Type–Specific Antibodies in Eperimentally Infected Chimpanzees", Proc. Natl. Acad. Sci. USA, 85:4478–4482 (1988).
Palker et al., "Polyvalent Human Immunodeficiency Virus Synthetic Immunogen Comprised of Envelope gp120 T Helper Cell Sites and B Cell Neutralization Epitopes", Journal of Immunology, 142:3612–3619 (1989).
Guy et al., "HIV F/3' orf encodes a Phosphorylated GTP–binding Protein Resembling an Oncogene Product", Nature, 330:266–269 (1987).
Culmann et al., "An Antigenic Peptide of the HIV–1 NEF Protein Recognized by Cytotoxic T Lymphocytes of Seropositive Individuals in Association With Diffrent HLA–B Molecules", Eur. J. Immunol., 19:2383–2386 (1989).

*Primary Examiner*—Lynette F. Smith
*Attorney, Agent, or Firm*—Finnegan, Henderson, Farabow, Garrett & Dunner, L.L.P.

[57] ABSTRACT

Compositions comprise one or more B epitopes of the envelope glycoprotein of a retrovirus and one or more T epitopes of the envelope glycoprotein from a distinct retrovirus, or a T epitope from a different protein of the same retrovirus as the B epitope. In particular, the retrovirus is a human immunodeficiency virus (HIV) or a simian immunodeficiency virus (SIV), human T-cell lymphotropic virus type 1 (HTLVI), or human T-cell lymphotropic virus type II (HTLVII).

21 Claims, No Drawings

COMPOSITION CONTAINING A B EPITOPE OF THE ENVELOPE GLYCOPROTEIN OF A RETROVIRUS AND A T EPITOPE OF ANOTHER DISTINCT PROTEIN OF THIS RETROVIRUS

This application is a continuation, of application Ser. No. 07/939,576 filed Sep. 3, 1992, now abandoned which is a continuation of Ser. No. 07/821,880 filed Jan. 17, 1992, now abandoned, which is a continuation of Ser. No. 07/659,422, filed as PCT/FR90/00620 Aug. 17, 1990 published as WO91/02544 Mar. 7, 1991, now abandoned.

The invention relates to compositions resulting from the reuniting of one or more B epitope(s) of the envelope glycoprotein of a lentivirus, in particular a retrovirus capable of inducing an AIDS in its natural host or a virus of the HTLVI or HTLVII type, and one or more T epitopes derived from a protein or glycoprotein of a retrovirus of the same type, other than the glycoprotein encoded by the env gene.

The invention also relates to vaccinating compositions utilizing these molecules.

Hitherto, the agents used to make up compositions having protective vaccinating properties towards an infection by a retrovirus capable of inducing an AIDS in its natural host have not proved to be satisfactory. The development of vaccinating compositions raises many problems. Among the most important problems, mention may be made of the fact that the virus may remain in the latent state after infection for a very long time, probably in the state of a provirus integrated into the genome of the cell hosts. The problems due to the considerable genetic variability of this virus may also be mentioned, in particular at the level of the surface envelope glycoproteins (env) gp160 and gp120, at the level of their structural proteins, in particular the gag protein as well as non-structural proteins such as the regulatory proteins, for example the products of the genes tat, rev, nef, vpr, vpu and/or vpx.

For semantic convenience, the proteins or glycoproteins will sometimes be designated in the following description by the abbreviation which identifies the genes which respectively encode them.

It will also be recalled that the HIV retroviruses are classed mainly into two different sub-types, HIV-1 and HIV-2 and that there exists within each of these sub-types many variants, some of which exhibit sequence differences which may exceed 25%. Another problem results from the capacity of the HIV retrovirus to elude the immune response, for example by spreading from cell to cell, thus avoiding the neutralizing antibodies, or also by remaining in the latent state for long periods. Furthermore, antibodies directed against a protein or a glycoprotein of a retrovirus capable of causing a LAS or an AIDS, in particular the HIV and SIV retroviruses, for example anti-gp120 antibodies and which do not have sufficient neutralizing properties, would be likely to promote the propagation of the virus through the intermediary of the binding of the virus-IgG complexes to the Fc receptors of the macrophages.

In addition, an efficacious vaccinating composition should lead to the rapid neutralization of the HIV virus, in the light of the fact that HIV multiplies in the T4 lymphocytes and kills these same cells, these latter being activated by contact with specific antigens and thus constituting an important aspect of the immune response.

The invention relates to a composition comprising at least one peptide, preferably a set of peptides, derived from the sequence of the envelope glycoprotein of at least one human immunodeficiency virus (HIV) or simian immunodeficiency virus (SIV), or a human T-cell lymphotropic virus type I or a human T-cell lymphotropic virus type II. Each peptide corresponds to a B epitope of the HIV or SIV. Additionally, the composition comprises at least one sequence of amino acids encoding a protein having a B epitope of at least one HIV, SIV, HTLVI or HTLVII, wherein the protein is other than the external envelope glycoprotein of the corresponding HIV, SIV, or HTLV retrovirus. The B and T epitopes are associated in the composition under conditions enabling them to interact or, preferably, the epitopes are combined by covalent or non-covalent coupling. For example, the two epitopes can be incorporated into a common recombinant structure or molecule obtained by genetic engineering or physical coupling by hydrophobic interactions. For semantic convenience, the products of combination will be referred to as "hybrid molecules."

It should be pointed out that the "B epitopes" correspond to the sequence (or one of the sequences) of amino acids which, within an immunogenic protein, is implicated in the production of antibodies, preferably neutralizing antibodies, against the corresponding retrovirus in the host to which this immunogenic protein is administered.

The T epitopes act by stimulating the immune system of the host. They can be detected in particular owing to their capacity to induce the proliferation of host lymphocytes placed in contact with them when the latter are placed in culture (cell proliferation assay).

The invention also relates to the use of these hybrid molecules for the manufacture of protective vaccines against infection by a lentivirus, in particular by a retrovirus of the IV or HTLVI or II type, and preferably against infection by any one of the retroviruses, distinct as they are one from the other, on account of the variability emphasized above, even of their belonging respectively to several possible sub-types. The invention also relates to a procedure for the preparation of the said hybrid molecules or vaccinating compositions containing several hybrid molecules of this type, these latter then being distinguished from each other by B epitopes, even T epitopes corresponding respectively to distinct peptide sequences themselves derived from the above-mentioned distinct retroviruses.

In each of the hybrid molecules according to the invention the immunogenic peptide containing one or several B epitopes derived from the env glycoprotein of the IV retrovirus, in particular HIV or HTLVI or II, may be combined with a carrier amino acid sequence bearing one or several T epitopes derived from one or more structural or non-structural proteins of either the same IV or HTLV, or a IV or HTLV, the env glycoprotein of which cross-reacts immunologically with that of the former.

It must be understood that what is said in what follows with regard to a defined "hybrid molecule" can be immediately transposed to other "hybrid molecules" capable of being associated with the former in vaccinating compositions of the type indicated above.

By "amino acid sequence" bearing the T epitope is understood either any part of the protein which contains it and which may extend so as to include the entire protein from which the T epitope is derived, this protein (or part of the protein) then being able to play the role of protein carrier, or a much shorter peptide, in particular limited to the sequence for the T epitope, this peptide then being capable of being linked itself through the intermediary of a covalent or non-covalent bond to a separate carrier molecule. This carrier molecule (when it is present) must then, owing to the sufficiently high molecular weight that it must then exhibit, contribute to the amplification of the capacity of the immune system of the host in which the composition is designed to produce protective antibodies oriented against the B epitopes, without interfering immunologically with the immune mechanisms stimulated by the above-mentioned B and T.

In a particularly preferred embodiment of the invention, the hybrid molecules corresponding to the former definition are characterized in that the immunogenic peptide bearing the B epitope and the carrier sequence of amino acids bearing the T epitope are chemically linked.

A first class of hybrid molecules of the invention is characterized in that the peptide containing the B epitope corresponds to the major neutralization epitope of the envelope glycoprotein of HIV-1 or to a part of this epitope, which is sufficient to conserve the properties of a "B epitope" as defined above. A second class of hybrid molecules comprises a peptide containing the B epitope corresponding to the major neutralization epitope of another HIV or SIV, HTLVI or HTLVII retrovirus. In an advantageous manner, the above hybrid molecules contain several B epitopes corresponding to the major neutralization epitope.

The major neutralization epitope of HIV-1 in particular is derived from a peptide sequence containing from about 20 to 30 amino acids of the sequence located in the loop which this major epitope forms in a hypervariable region of the envelope glycoprotein of the HIV-1 retrovirus. This major neutralization epitope of HIV-1 has been described by PUTNEY S. D. et al. 1986 (Science 234, 1392–1395) and by RUSCHE J. R. et al. 1988 (Proc. Natl. Acad. Sci., USA, 85, 3198–3202). This major neutralization epitope is sometimes designated as "Putney peptide". It is, in particular, the sequence extending approximately from the 301th to the 336th residue of the amino acid sequence of the envelope glycoprotein of the HIV-1 retrovirus Bru as described in the monograph: Human Retroviruses and AIDS, 1989 Myers, Rabson, Josephs, Smith, Berzofsky, Wong, Staal Edition "Los Alamos National Laboratory".

Also included in the scope of the invention for the formation of hybrid molecules are the peptides containing a B epitope corresponding to the major neutralization epitope of the envelope glycoprotein of another variant of HIV-1 or also of another HIV retrovirus, for example HIV-2, or also a virus showing immunological relatedness to a HIV retrovirus, for example the SIV virus or another lentivirus such as HTLVI or HTLVII. These peptides may be obtained by taking the amino acid sequence of the variant or of the selected retrovirus corresponding to the sequences defined above.

According to an advantageous embodiment of the invention, particular hybrid molecules of the invention may contain, in order to form the carrier peptide of the B epitope, the peptide regions of the envelope glycoprotein of HIV-1BRU comprising in particular the amino acids 267 and 128. The length of these peptide regions is determined as a function of the capacity of the peptide region thus defined to participate in the formation of a functional major neutralization epitope.

The invention also relates to the corresponding peptide regions of a variant different from HIV-1 BRU, or the peptide regions of another HIV retrovirus or of another related lentivirus implicated in the constitution of the major neutralization epitope.

The hybrid molecules of the invention have the interesting property of being capable of inducing a good immune response implicating the T cells and they would be expected to be capable of triggering a good primary immune response. Furthermore, should the vaccinated subject subsequently be in contact with the virus, the booster effect would probably be triggered by the intermediary of the T cells with a memory enabling them to recognize the T determinants of the antigens of the virus.

In what follows recourse is had to the nomenclature for designating the amino acids by one letter. It should be recalled that a peptide containing the B epitope comprises, in particular, a part of the major neutralization epitope of the env glycoprotein of HIV or SIV, sufficient in size to induce or participate in a protective immune response.

The sequences given below are identified by using the 1-letter code, the correspondences of which with the amino acids are given below:

| | |
|---|---|
| Alanine | A |
| Arginine | N |
| Asparagine | N |
| Aspartic Acid | D |
| Cysteine | C |
| Glutamine | Q |
| Glutamic Acid | E |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

In a particularly advantageous manner, a hybrid molecule according to the invention is characterized in that the peptide containing the B epitope comprises at least one of the following sequences or a part of these sequences comprising the B epitope:

NTRKR IRIQRGPGRA FVTIGK-IGN
NTRKS IRIQRGPGRA FVTIGK-IGN
NTRKK IRIQRGPGRA FVTIGK-IGN
NTRGS IRIQRGPGRA FVTIGK-IGN
NTRKS IYI--GPGRA FHITGRIIGD
NVRRS LSI--GPGRA FRTRE-IIGI
NTRRG IHF--GPGQA LYTTGIV-GD
NTRQR TPI--GLGQS LYTTRSR-SI
NTRKS ITK--GPGRV IYATGQIIGD
NTRKR ITM--GPGRV YYTTGQIIGD
DKRQS TPI--GLGQA LYTTRGRTKI
DKKIR QSIRIGPGKV FYAKGG---I
NTKKG IAI--GPGRT LYAREKIIGD
HTRKR VTL--GPGRV WYTTGEILGN
NTRRG SHF--GPGQA LYTTGIVGDI
KITSRQTPI--GLGQA LYTTRIKGDI
NVRRR HIHI-GPGRA FYTGEIRNI
NTRQS TPI--GLGQA LYTTRTKSI
NTTRS IHI--GPGRA FYATGDIIGTI
NKRKR IHI--GPGRA FYTTKNIIGDI

In the preceding peptide sequences and in those which follow, the dashes (when they are present) represent direct linkages. Their presence is intended to maintain in vertical alignment sequences which show an at least partial homology among the various IVs from which the said peptides are derived.

Another particularly advantageous hybrid molecule is characterized in that the carrier peptide of the B epitope comprises at least one of the following sequences or a part of these sequences comprising the B epitope:

TRPNNNTRKR IRIQRGPGRA FVTIGK-IGNM-RQAH
TRPNNNTRKS IRIQRGPGRA FVTIGK-IGNM-RQAH
TRPNNNTRKK IRIQRGPGRA FVTIGK-IGNM-RQAH
TRPNNNTRGS IRIQRGPGRA FVTIGK-IGNM-RQAH
TRPNNNTRKS IYI--GPGRA FHTTGRIIGD -IRKAH
TRPYNNVRRS LSI--GPGRA FRTRE-IIGI -IRQAH
TRPGNNTRRG IHF--GPGQA LYTTGIV-GD -IRRAY
ARPYQNTRQR TPI--GLGQS LYTTRSR-SI -IGQAH
TRPNNNTRKS ITK--GPGRV IYATGQIIGD -IRKAH
TRPNNNTRKR ITM--GPGRV YYTTGQIIGD -IRRAH
TRPGSDKRQS TPI--GLGQA LYTTRGRTKI -IGQAH
TRPGSDKKIR QSIRIGPGKV FYAKGG---I -TGQAH
TRPNNNTKKG IAI--GPGRT LYAREKIIGD -IRQAH
TRPNNHTRKR VTL--GPGRV WYTTGEILGN -IRQAH
TRPGNNTRRG SHF--GPGQA LYTTGIVGDI -RRAY
TRPDNKITSRQ-TPI-GLGQA LYTTRIKGDI -RQAY
TRPNNNVRRR-HIHI-GPGRA FYTGEIRNI -RQAH
TRPYKNTRQS-TPI--GLGQA LYTTRTKSI -GQAH
TRPNNNTTRS-IHI--GPGRA FYATGDIIGTIRQAH
TRPNYNKRKR-IHI--GPGRA FYTTKNIIGDIRQAH

Preferred immunogenic compositions containing several of the hybrid molecules conforming to the invention differ from each other with respect to their B epitopes, indeed with respect to the whole of their respective epitopes, preferably such a composition comprises all of the sequences described above or a combination of several of these sequences.

For coupling the peptides described above to the carrier molecules, recourse is advantageously had to an amino acid such as cysteine or tyrosine placed at the beginning or end of the peptide which it is desired to couple.

Preferred compositions contain all or almost all of the hybrids containing respectively the B epitopic sequences which are the subject of the list cited above.

Other preferred compositions contain hybrids containing the B epitopic sequences combined with the peptide regions corresponding to the parts of the major epitope comprising the amino acids 267 and 128 in the case of HIV-1 BRU or the peptide regions having the same function in another lentivirus such as HIV-2, SIV, HTLVI, HTLVII.

Other useful compositions of epitopes contain a T epitope characteristic of a defined virus in combination with the B epitopes of this virus and of its variants.

Other hybrid molecules complying with the general definition already given are characterized in that they comprise at least one minor neutralization epitope, in particular an epitope derived from a conserved region of the envelope glycoprotein of HIV or SIV.

The term minor neutralization epitope refers to peptide sequences belonging to the envelope glycoprotein of HIV or SIV retrovirus or another of the viruses mentioned above, characterized in that they belong to a conserved region of the env glycoprotein, in that they contain a B epitope and in that they induce neutralizing antibodies when they are injected into an animal.

A hybrid molecule containing such a minor neutralization epitope associated or combined with at least one T epitope under the above-mentioned conditions thus has the role of inducing in vivo antibodies capable of neutralizing several variants or strains of distinct viruses, even of neutralizing several distinct retroviruses.

In a particularly preferred manner, the hybrid molecules containing these minor neutralization epitopes are associated with one or more hybrid molecules containing one or preferably several of the major neutralization epitopes as described previously, even all of these latter hybrid molecules.

By conserved region is meant a domain of the envelope glycoprotein which has conserved about at least 85% of its amino acids among the various strains of HIV.

In a particularly preferred embodiment of the hybrid molecules of the invention, the minor epitope comprises for example one of the following sequences, the first two described by Chanh et al. in The EMBO Journal vol. 5, No. 11, p. 3065-3071, 1986 and the last two described by HO et al. in Science, vol. 239 26 Feb. 1988 p. 1021-1023:

YDRPEGIEEEGGERDRDRSG
VAPTKAKRRVVQREKRAVGIGALFLGFLGAG
CTHGIRPVVSTQLLLNGSLAE
STQLLLNGSLAEEEVVIRC

The amino acid sequence bearing the T epitope included in the composition of the hybrid molecules according to the invention is derived from the protein encoded in the nef gene ("nef protein") or from a gag protein, and even from a protein selected from among those which are encoded in the tat, rev, vif, pol, vpr, vpu and vpx genes. They advantageously contain from 6 to 15 amino acids. The nomenclature of the genes contained in HIV and SIV is described in "Nature" vol. 333-9 June 1988, Gallo et al.

According to a particularly preferred embodiment of the hybrid molecules, the carrier sequence of amino acids is derived from the protein encoded in the nef gene or from a derived antigen.

The protein encoded in the nef gene is a regulatory protein which shows an immunogenicity for the cytotoxic and helper T lymphocytes (CTL). This non-structural protein is absent from infectious HIV virions and may be detected in the cytoplasm of cells infected by HIV. The detection of the expression of the nef protein at the cell surface, either by immunofluorescence or by other serological methods has proved to be difficult. The nef protein probably undergoes maturation in the cytoplasm of the producing cell and is exported to the cell surface in the form of oligopeptide fragments recognized by the cytotoxic T lymphocytes. The cytotoxic T lymphocytes specific for the human HIV retrovirus comprise several sub-populations, one of which is specific for the nef protein. The nef protein has been described in an article by Guy et al. Nature 1987, 330:266 and in the patent application EP. 0253693 (87.401.388.6 of Jun. 15, 1987).

By derived antigen is meant any molecule resulting from a modification of the original protein or from a cleavage of this protein which does not adversely affect the T epitope which it contains.

Advantageously, the sequence of amino acids bearing a T epitope may be selected from the following group of peptides derived from the nef protein (protein F) of LAV-BRU (HIV-1 BRU) or also comprises all or part of the amino acid sequences of these peptides, for example:

FP 16 peptide of the F protein consisting of 16 amino acids (residues 171-205)

GMDDPEREVLEWRFDSRLAFHHVARELH-PEYFKNC

FP 17 (residues 141–205)

CYKLVPVEPDKVEEANKGENTSLLHPVS-
LHGMDDP

EREVLEWRFDSRLAFHHVARELHPEYFKNC

FP 63 (residues 185–205)

DSRLAFHHVARELHPEYFKNC

Another group of peptide carriers of a T epitope comprises the following characteristic nef peptides of LAV-BRU.

FP 15 (residues 118–167)

CGYFPDWQNYTPGPGVRYPLTFGW-
CYKLVPVEPDK

VEEANKGENTSLLHPV

FP 18 (residues 93–122)

CKGGLEGLIHSQRRQDILDLWIYHTQGYFPD

Similarly, the invention applies to the corresponding sequences of the other isolates of HIV-1 and of the other HIV or SIV retroviruses.

Other amino acid sequences bearing a T epitope may constitute carrier sequences for the construction of the hybrid molecules. For example, one attractive possibility is to use a gag protein, in particular a P55, P25, P18 or P12 protein of HIV-1, or also a protein encoded in the gag gene of HIV-2 or SIV, or a fragment of these proteins encoded in the gag gene, provided that they bear a T epitope, or a composite preparation of several of these proteins and/or fragments.

Proteins other than the proteins specific for the HIV retroviruses or related retroviruses such as SIV, HTLVI, HTLVII may also be used in the production of hybrid molecules conforming to the invention as carrier molecules of the above-mentioned B and T epitopes. For this purpose recourse may advantageously be had to certain constitutive antigens of hepatitis B virus particles, for example the HBs or HBc antigens, tetanus toxoid or also hemocyanin (KLH) or human albumin (HSA) etc. The carrier molecules just mentioned only represent preferred examples among other possible choices. One criterion for determining the possibility of using another molecule is, for example, its compatibility with the HLA haplotype of the recipient of the vaccinating composition comprising the said hybrid molecules.

Amino acid sequences included in the composition of the hybrid molecules may thus also result from the chemical coupling of a peptide bearing a T epitope derived from a protein encoded with one of the genes tat, rev, vif, pol, vpr, vpx, vpu, gag or nef or of a derived antigen to the carrier molecule, in particular the HBs antigen, the HBc antigen, tetanus toxoid, hemocyanin and human albumin.

The construction of the hybrid molecules of the invention with the aid of a sequence containing at least one B epitope and a carrier sequence containing at least one T epitope may be carried out by coupling of these sequences. Hybrid molecules may also be constituted by an association in one and the same composition of the various sequences described previously.

They may also result from the expression of a recombinant DNA comprising both a nucleotide sequence coding for an immunogenic peptide containing a B epitope and derived from the env glycoprotein derived from a IV, a HTLVI or a HTLVII, and a sequence coding for an amino acid sequence containing at least one T epitope such as defined above, where appropriate under the control of a promoter making possible its expression in a defined host selected, for example, from among bacteria, yeasts, viruses or eucaryotic cells.

The peptides used to construct the hybrid molecules of the invention may be prepared by the standard techniques used in the field of peptide synthesis. This synthesis may be carried out in homogeneous solution or on a solid phase.

For example, recourse may be had to the procedure of synthesis in homogeneous solution described in the standard work HOUBENWEYL entitled "Methode der Organischen Chemie" (Methods in Organic Chemistry), edited by E. W ünsch, vol. 15-I and II. THIEME, Stuttgart 1974.

Furthermore, the invention relates to a procedure for the preparation of hybrid molecules described above in which the sequences containing the B epitopes and the sequences containing the T epitopes are coupled by chemical means, this procedure comprising in particular the reaction of amino acid sequences containing the T epitope with one or more peptides bearing the B epitope in the presence of a coupling agent selected according to the reactive functions implicated in this coupling, the other reactive functions which may be present being protected as necessary followed by the recovery, after deprotection of the protective functions where necessary, of the products of coupling obtained now bearing the said B and T epitopes.

The coupling systems making it possible to link together the different amino acid sequences will be selected as a function of the nature of the terminal residues of the said amino acid sequences. As an example, when the terminal residues are cysteines, the coupling with lysine residues may be carried out by using SPDP (N-succinimidyl-3-(2-pyridylthio)-propionate, or sulfo-MBS described by Lerner et al in (Nature, October 1980, p801 to 805, vol. 287) or other bifunctional reagents.

When the coupling implicates tyrosine residues, other coupling reagents may be used. When the residues to be coupled are lysine residues, it will be possible to use glutaraldehyde.

In order to produce hybrid molecules in conformity with the invention, this procedure consists of reacting a first peptide containing a first type of reactive function with a second peptide (or several peptides) containing another reactive function (or several reactive functions) complementary to that of the first peptide, the additional reactive functions possibly present in some of these peptides and not involved in the reaction (or reactions) being protected if necessary. It is understood in this context that "complementarity" means the capacity of the reactive functions of two distinct peptides to lead to a direct or indirect, covalent coupling reaction if necessary in the presence of a reagent which is also bifunctional or simply of a chemical reagent which promotes the covalent coupling reaction.

Preferably, the first peptide contains at least one amine, free carboxyl, ester or alcoholic function capable of participating in a coupling reaction with a corresponding function borne by the second peptide.

In conformity with a first variant of the procedure according to the invention, the condensation between a first peptide bearing at least one free amine function and a second peptide also bearing at least one free amine function is carried out and the condensation of these two peptides is performed in the presence of a bifunctional reagent such as, for example, glutaraldehyde or benzoquinone.

According to another variant of the procedure of the invention, the first peptide bearing a reactive amine, carboxyl, hydroxyl or sulfhydryl function is reacted according to one of the procedures currently used in peptide synthesis with the second peptide which itself also bears a complementary reactive amine, carboxyl, hydroxyl alcohol or sulfhydryl function.

When the coupling is carried out between a carboxyl function borne by one of the partners with an amine function borne by the other partner to the reaction, the reaction is advantageously carried out in a aqueous phase in the presence of a water-soluble carbodiimide or of a lipid-soluble carbodiimide in an inert organic solvent such as dimethyl formamide (DMF) or tetrahydrofuran (THF), ethyl acetate, methylene chloride etc.

Useful water-soluble carbodiimides are N-cyclohexyl-N'-beta-(N-methyl-morpholino)-ethyl) carbodiimide p-toluene sulfonate, (3-ethyl)-aminopropyl-carbodiimide hydrochloride.

A carbodiimide suitable for reactions carried out in an organic solvent is, for example, N,N'-dicyclohexyl-carbodiimide.

According to another variant of the procedure according to the invention, the carboxyl function borne by one of the partners is reacted with an alkyl chlorocarbonate ($C_2$ to $C_4$), then the mixed anhydride obtained with this first partner is reacted with the second partner bearing the amine function which must participate in the coupling carried out in an inert organic solvent, such as described above, or in an aqueous phase.

The first step of the reaction is carried out, for example, in dimethylformamide in the presence of a tertiary amine, for example N-methyl-morpholine, by using, for example, isobutyl chlorocarbonate. After three minutes at $-16°$ C., the partner bearing an amine function deprotonated, for example, by means of N-methyl-morpholine is added to the reaction mixture.

According to a third variant of the procedure according to the invention, an active ester formed from the partner bearing the carboxyl group participating in the coupling reaction is reacted with the other partner bearing an amine function. Useful activated esters are the para-nitrophenyl ester and the N-hydroxysuccinimide ester.

Where necessary, these reactions are carried out in an inert organic solvent, such as dimethyl formamide.

According to yet another variant of the procedure according to the invention, one of the partners bearing a sulfhydryl function is reacted with the other partner which bears a maleimide group.

It is also possible to react the partner bearing the sulfhydryl group with the other partner bearing a 6-maleimido-caproic acid group or a 3-(2-pyridyl-dithio) propionate group.

The reactive functions not required to participate in the reaction may be protected by standard protecting groups.

The carboxyl groups may, in particular, be protected by benzyl, benzylidene or anizilidene groups.

These ester groups may then be removed, in particular, by hydrogenolysis. Furthermore, this latter process also enables other protecting groups such as N-carbobenzoxy groups to be removed simultaneously.

The amine functions are advantageously protected by benzyloxycarbonyl, t-butoxycarbonyl or toluene sulfonyl groups. These groups may then be removed by controlled catalytic hydrogenation, for example in the presence of palladium, or by acidolysis or also by the action of sodium in liquid ammonia.

The sulfhydryl functions not participating in the coupling reaction may be protected by acetamidomethyl or formamidomethyl groups.

Of course, it is possible to have recourse to any other type of linkage involving the combinations which may occur between a sulfhydryl function borne by one of the partners and a maleimide group borne by the other partner, for example by making use of the technique described by T. KITAGAWA and T. AIKAGAWA in "J. Biochem." 79 (1976), 233.

The conjugation may also be carried out by using the standard methods of diazotisation or reaction involving an isothiocyanate, in particular when one of the peptides bears an aromatic amine function and when the other peptide bears an amine function capable of participating in this reaction. Such preparative procedures are described, for example, by B. F. ERLANGER in "Pharmacol. Rev" 25 5 1973, p. 271.

The coupling may also be carried out by the reduction of a Schiff base formed between an aldehyde function borne by one of the peptides and an amine function borne by the other peptide (for example according to the technique of G. R. GRAY, "Arch. Biochem. Biophys.", 163 (1974), p. 425).

All of these reactions are in themselves well known and the person skilled in the art will realize that very many variants may be adapted to give the same results. It should also be noted that the conjugations between peptides may be carried out by means of a bridge, the bridging agent consisting for example of a bifunctional reagent. In this case, the bridging group between two peptides in the final conjugate preferably will not exceed a chain length corresponding to that of a chain of ten carbon atoms.

Such bridging agents are, for example, mentioned in the patent FR No. 78/16792 filed on 5 Jun. 1978.

In all of the foregoing reactions, the relative proportions of the peptides used may be varied according to the final proportions of each peptide desired in the final hybrid molecule. In particular, these relative proportions are adjusted in relation to the number of functional groups borne by each of them and capable of entering into the conjugation reaction with complementary functional groups.

The hybrid molecules according to the invention may also be produced by genetic engineering by the expression in a suitable cell host of a recombinant DNA containing both at least one nucleic sequence coding for an immunogenic peptide derived from the env glycoprotein and bearing the B epitope and a nucleic acid sequence coding for the sequence of amino acids bearing the T epitope, the whole being under the control of regulatory elements permitting its expression in a selected competent host, for example a yeast, a bacterial strain or a line of eucaryotic cells, and by recovering and subsequently purifying the expression products obtained.

The invention also relates to a vaccine composition comprising several hybrid molecules of the invention. Preferred compositions contain an association of hybrid molecules corresponding to all of the hybrid molecules containing the particular sequences of amino acids given for the B epitopes.

The invention also relates to immunogenic compositions capable of inducing in vivo the production of protective and/or neutralizing antibodies towards a pathogenic IV retrovirus, in particular towards a pathogenic HIV or also a HTLVI or a HTLVII, characterized in that they contain as active ingredient the hybrid molecules of the invention, in combination with an acceptable pharmaceutical vehicle.

The immunogenic compositions of the invention are advantageously administered in the form of mixtures containing the active ingredient with an immune adjuvant.

They can be administered, for example, by injection, by the parenteral route.

Advantageously, the immunogenic compositions according to the invention contain in addition a vehicle facilitating the administration of the vaccine. Such vehicles are for example: polyvinylpyrrolidone, or any known adjuvant i.e. any substance facilitating the absorption of the medicine or its action in the organism.

As examples of other adjuvants of this latter type mention should also be made of carboxymethyl-cellulose, the hydroxides and phosphates of aluminium, or all other adjuvants of this type well known to the person skilled in the art. Finally, the immunogenic compositions contain, if necessary, an immunological adjuvant, in particular of the muramyl peptide type, or the Syntex adjuvant described by Allison et al, in particular in the "Proceeding book— colloque des Cent Gardes —October 1986-PARIS-FRANCE".

The invention also relates to the use of the hybrid molecules as antigens in compositions for the diagnosis of the presence of antibodies resulting from an infection by a IV, HTLVI or HTLVII retrovirus. Such compositions may be used on a sample consisting, for example, of a patient serum and it is possible, for example, to have recourse to the ELISA techniques to carry out the detection.

The invention also relates to the DNA and RNA nucleotide sequences coding for the peptide sequences previously described and, in particular, for the peptide sequences of the preferred B epitopes.

These nucleotide sequences may be used in the form of probes or also may be included in the composition of probes for the diagnosis of an infection by a HIV retrovirus.

In a particular embodiment of the in vitro diagnosis of an infection by a retrovirus the techniques of genetic amplification are used, the said probes being used as primers. In this respect reference may be made to the techniques described in the European patent application published under the numbers 0200362 (EP 86.302.298.4 of 27 Mar. 1986) and 0229701 (EP 87.300.203.4 of 9 Jan. 1987) as well as the EP application published under the No. 0283327 (EP 88.400.084.5 of 15 Jan. 1988).

The invention relates in particular to a recombinant DNA characterized in that it comprises a first nucleotide sequence coding for an immunogenic peptide derived from the env glycoprotein and contains a B epitope and a second sequence of amino acids coding for a T epitope derived from a protein of the HIV different from the env glycoprotein, where appropriate under the control of a promoter making possible the expression of the above-mentioned first and second sequences in the form of a hybrid molecule in a defined host selected, for example, from yeasts, viruses, bacteria or eucaryotic cells. It also relates to a cell host transformed by the said recombinant DNA characterized in that it is a yeast, a virus, for example a baculovirus, a pox virus, an adenovirus or a herpes virus, or a eucaryotic cell or a bacterium, for example *E. coli*.

Other advantages and characteristics of the invention will become apparent in the examples which follow:

EXAMPLE 1

Purification of the recombinant protein p18 of HIV-1 produced by a *Escherichia coli* strain A procaryotic plasmid for the expression of p18 of HIV-1 (pTG2153) is constructed in the following manner:

the bacteriophage M13TG1154 (Rautmann G. et al. AIDS Res. & Human Retroviruses 5 p117–157) carries the complete gag gene in which the TAC codon coding for the last amino acid of p18 has been replaced by the stop codon TAG. A BglII restriction site is introduced immediately upstream from the gene coding for p18 by directed mutagenesis with the aid of the following oligonucleotide:

5' CTCGCACCCATAGATCTCCTTCTAG 3' in order to give the bacteriophage M13TG1161.

a BglII-PstI fragment containing the gene coding for p18 is introduced into the procaryotic expression vector pTG959, the construction of which is described in the patent application EP-0292404, carrying the PL promoter of the lambda bacteriophage N a synthetic sequence (ribosome binding site) cII, lacz and ampR. This insertion is made after digestion of pTG959 by BglII and PstI which removes the cII sequence. In this way the plasmid pTG2153 is obtained.

The *E. coli* strain 901 is then transformed by this procaryotic plasmid for the expression of p18. The p18 gene is then found under the control of the PL promoter regulated by its thermosensitive repressor. After about 2.5 hours of growth at 30° C. (to give a O.D. of 0.3 at 550 nm), increasing the temperature of the culture medium to 42° C. induces the expression of the p18 protein. After 7 hours (O.D. about 2.4) at this temperature, the cells are harvested by centrifugation (10 min. at 5000 revs/min). The pellet is taken up in PBS buffer.

The recombinant protein p18 is released from the cells after freezing to −80° C. followed by thawing at 0°–2° C. or by sonication. Centrifugation is then carried out (20 min. at 10000 revs/min) and the supernatant is recovered. These two operations are repeated before the protein is purified.

The recombinant protein p18 is purified by cation exchange chromatography on Sepharose followed after dilution (in order to obtain a conductivity identical with that of PBS) by strong cation exchange HPLC with a yield of about 20%.

The recombinant protein p18 thus obtained is then characterized by SDS-PAGE electrophoresis, reverse phase HPLC and by determination of its amino acid sequence by making peptide maps before and after cleavage by trypsin or the V8 protease of *Staphylococcus aureus*. These verifications confirm that the sequence of the recombinant protein p18 is in conformity with that predicted by the analysis of the nucleotide sequence of the complementary DNA used. It is recognized by monoclonal antibodies specific for p18 of HIV-1 (Chassagne J. et al., J. Immunol. (1986) 186 p14442).

The recombinant protein p18 possesses a degree of purity of 90%, it may be stored in phosphate buffer/NaCl at −80° C. and remains stable.

EXAMPLE 2

Purification of the recombinant protein p25 of HIV-1 produced by an *Escherichia coli* strain The procaryotic plasmid for the expression of p25 of HIV-1 (pTG2103) is constructed in the following manner:

the bacteriophage M13TG1124 described in the patent publication EP-0276591 contains a reading frame which codes for a protein P25 extended at its N-terminus by two additional amino acids: a methionine followed by a glycine. The remainder of the sequence is absolutely identical with that of P25 of HIV-1. A BglII site is introduced as is an alanine codon at the N-terminus of the reading frame of P25 (by replacement of the glycine) by means of directed mutagenesis with the aid of the following oligonucleotide:

5' TAGGTGCCATAGATCTGACCTGGA 3' in order to produce the phase M13TG1126.

a BglII-EcoRI fragment of M13TG1126 is introduced into the pTG959 plasmid digested by BglII and EcoRI to give the procaryotic plasmid for the expression of P25, pTG2103.

The *E. coli* strain 901 is then transformed by this expression plasmid for P25. The P25 gene is then found under the control of the PL promoter regulated by its thermosensitive repressor. After about 2.5 hours of growth at 30° C. (to give a O.D. of 0.3) increasing the temperature of the culture medium to 42° C. induces the expression of the P25 protein. After 7 hours (O.D.=2.4) at this temperature, the cells are harvested by centrifugation (10 min. at 5000 revs/min).

The recombinant P25 protein is extracted from the cytosol fraction after sonication or by means of a "French-press". The supernatant is dialysed/diafiltered against a buffer of low ionic strength (20 mM Tris/HCl, pH 8). Most of the E. coli proteins are adsorbed on a weak anionic change support. The P25 protein is found in the non-adsorbed fraction with a purity of about 80%. This fraction is subjected to chromatography on a Sepharose metal chelate (loaded with $Zn^{2+}$) and equilibrated with a low ionic strength Tris buffer (20 mM) at pH 8. The p25 protein is released by means of a linear glycine gradient (0–200 mM, pH 8), followed by a step employing 500 mM of imidazole, pH 8.

Instead of the chromatography using a metal chelate, it is possible to carry out chromatography on TSK orange. This step may also be carried out as an additional step of purification. The protein is then dissolved in a low ionic strength Tris buffer, pH 8. Elution is performed using a linear gradient of NaCl (0–1M).

The fractions rich in p25 are pooled, reduced at room temperature with 40 mM of beta-mercaptoethanol and diafiltered against 170 mM of NaCl, 20 mM of sodium phosphate, pH 7. The recombinant protein p25 thus purified possesses a purity higher than 90%. It may be stored at –80° C. without undergoing degradation.

The recombinant protein p25 is characterized by gel electrophoresis (SDS-PAGE), reverse phase HPLC, determination of the amino acid composition, analysis of the N- and C-terminal sequences after proteolytic digestion, isoelectric focussing and mass spectrometry.

EXAMPLE 3

Purification of the recombinant nef protein of HIV-1 produced by an *Escherichia coli* strain The production of the recombinant nef protein of HIV-1 by the TGE901 strain has been described in the patent application EP-0292404.

The recombinant nef protein is extracted from the cytosol fraction after sonication or by means of a "French-press". After centrifugation, the pellet and the supernatant are recovered and are subjected to various treatments.

the supernatant is treated with 35% $(NH_4)_2SO_4$ to give a precipitate, then is centrifuged at 10000 revs/min for 20 min. The pellet is recovered in HEPES-1 buffer (20 mM HEPES; pH 8; 50 µM GDP; 5 mM $Mg^{2+}$; 10 mM DTT; 100 µM EDTA: 100 µM EGTA; 100 µM $NaN_3$ and 100 µM PMSF).

The pellet is dissolved over a period of 12 to 16 hours at room temperature in an 8M urea solution, then is subjected to dialysis for 24 hours at 4° C. in HEPES-1 solution. After centrifugation at 10000 revs/min for 20 min., the supernatant is recovered.

The supernatants obtained in these two steps are subsequently treated in an identical manner.

First, anion exchange chromatography is performed on DEAE Sephadex equilibrated with HEPES-1. The nef protein is eluted by means of a NaCl gradient (0 to 1M), then the fractions rich in nef protein are subjected to affinity chromatography on Cibacron Blue F3GA Agarose equilibrated with the HEPES-1 buffer without DTT, EDTA and EGTA. The nef protein is then eluted by a NaCl gradient (0 0 1.5M) in HEPES-1 buffer, then the fractions rich in the nef protein are subjected to affinity chromatography on a metal chelate ($Zn^{2+}$) by using the HEPES-2 buffer (pH 7, 20 mM HEPES, 0.5M NaCl, 1 mM imidazole, 50 µM GDP and 100 µM $Mg^{2+}$).

The nef protein is eluted by means of an imidazole gradient (1 to 20 mM) and the fractions rich in the nef protein are diafiltered. It is then taken up in 20 mM HEPES buffer (pH 8, 50 µM GDP, 100 µM $Mg^{2+}$ and 5 mM DTT).

The recombinant nef protein thus isolated is analysed by means of Western blot. Its purity is higher than 95% as determined by reverse phase HPLC and 90% as determined by SDS-PAGE. The N-terminal sequence as well as its GTP binding activity were also checked and found to conform.

EXAMPLE 4

Covalent coupling of HIV peptides derived from the region of the glycoprotein forming a Putney loop to P18gag or to P27nef 2 mg of P18gag or P27nef in 4 ml of 0.1M phosphate buffer, 0.1M NaCl, pH 7.5 are treated by the addition of 20 µl of a 10 mg/ml solution of SPDP in ethanol. After 30 min. at 25° C., the mixture is passed over Sephadex G-25. The fractions excluded are taken up and mixed with the cocktail of 21 HIV peptides corresponding to the known 21 sequences of the Putney epitope each containing a cysteine on either side of this sequence and each present in an amount of 100 µg. The said cocktail had been previously reduced by treatment with β-mercaptoethanol 0–1M ammonium bicarbonate then rapidly lyophilized.

The mixture of P18 peptides or P27 peptides is incubated overnight at 25° C., then passed over Sephadex G-50 after centrifugation of the precipitate which formed overnight. The fractions excluded are taken up together with the precipitate and are injected into rabbits in 200 µg doses by the subcutaneous route in the presence of Freund's adjuvant (complete, then incomplete). The fractions injected were assayed by means of RIA in order to detect the presence of the peptides as described in the following example:

EXAMPLE 5

Covalent coupling of HIV-1 peptides to Bovine Serum Albumin (BSA)

1 mg of BSA (500 µg/ml in 0.1M phosphate-0.1 NaCl at pH 7.5) was mixed with N-succinimidyl-3-(2-pyridyldithio) -propionate (SPDP; 10% of 10 mg/ml of solution in ethanol) for 30 minutes at 25° C. The BSA derivatives were separated from the excess SPDP by exclusion chromatography on Sephadex G25. The fractions corresponding to the exclusion volume of the column were mixed with 1 mg of the peptide having cysteine residues and reduced with 2-mercaptoethanol (10 mg/ml) in 0.1M of ammonium bicarbonate. A rapid lyophilization was then carried out before they were used. The BSA mixture treated with SPDP and reduced peptides was kept overnight at 25° C., then chromatographed on a column of Sephadex G50. The fractions collected corresponding to the exclusion volume of the column were assayed in order to detect the presence of the peptides. For this purpose, polystyrene beads were coated with the recovered fractions diluted 10 fold in series in 0.1M Tris at pH 8.8 overnight at 20° C. The beads were then coated with BSA (10 mg/ml) and gelatin (2.5 mg/ml). The peptides bound to the beads were detected by RIA.

EXAMPLE 6

Epitope of the nef p27 recognized by the "helper" T lymphocytes

The particular specificity of the proliferative response of lymphocytes to the nef p27 protein was studied. A series of 14 synthetic overlapping peptides, covering the whole of the sequence of the product of the nef gene of HIV-1 LAV-BRU was assayed in order to detect their capacity to induce proliferative responses of peripheral blood lymphocytes (PBL) in two chimpanzees at different times after the injection of the nef antigen.

These chimpanzees received purified nef P27 mixed with the Syntex adjuvant based on MDP-Threonyl. 3 Injections were given at monthly intervals, followed by a booster at 6 months.

The peptide concentration necessary to observe an optimal response was first determined as being about 50 µg/ml, by using peptides whose capacity to induce a positive or negative response was known.

In independent assays, the lymphocytes of the chimpanzee 479 showed that they reacted strongly with the peptides PF16 (residues 171–205), PF17 (141–205) and PF63 (185–205). A weaker proliferation (less than 25 to 50% RR, Relative Response) was noted with two of the three samples of PBL towards the PF15 peptides (118–167) and with three of the four samples towards the PF18 peptides (93–122). No significant proliferation was detected in a reproducible manner with the other peptides used (table 1).

Comparable results were obtained with the PBL of the chimpanzee 433.

It was thus verified that none of the stimulating peptides was mitogenic, non-specific for the T cells at the concentration used: the PBL of the control chimpanzee (411) which was immunized only against the virus of the vaccine and which received repeated injections of adjuvant, did not proliferate in response to these peptides.

These data show that the recognition by the helper T cells of the 2 chimpanzees of at least 2 epitopes present on the T cells of the nef p27 protein: 1 epitope seems to be located within a sequence of 60 amino acids at the C-terminus of the molecule and more probably in the region of the last 20 amino acids as is shown by the antigenicity of PF63. The other epitope may be located in the vicinity of a region covering both PF18 and PF15 (109–122). These peptides are combined with advantage with B epitopes such as have been defined above.

TABLE 1

PROLIFERATIVE RESPONSES OF THE PBL OF THE CHIMPANZEE No. 479 to nef P27 (500 µg/ml) AND TO SYNTHETIC PEPTIDES (50 µg/ml) OF THIS PROTEIN RELATIVE RESPONSE TO P27 (%) A:

| Peptide | position a.a | week 4 | week 12 | week 14 (1) | week 41 |
|---|---|---|---|---|---|
| PF 12 | 1–66 | 37 | 12 | — | 21 |
| PF 11 | 1–31 | 0 | 16 | — | 12 |
| PF 3 | 1–17 | (2) | 0 | — | 3 |
| PF 5 | 17–35 | — | 2 | — | 0 |
| PF 13 | 32–64 | 8 | 17 | — | 11 |
| PF 6 | 35–52 | — | 0 | — | 5 |
| PF 14 | 65–109 | 13 | 28 | — | 13 |
| PF 8 | 88–105 | — | 0 | — | 0 |
| PF 18 | 93–122 | 29 | 42 | 51 | 20 |
| PF 15 | 118–167 | 28. | 40 | — | 25 |
| PF 17 | 141–205 | 71 | 155 | 222 | 81 |
| PF 62 | 147–172 | — | 5 | 0 | 3 |
| PF 16 | 171–205 | 98 | 174 | 59 | 52 |
| PF 63 | 185–205 | — | 78 | 125 | 54 |
| reactivity of PBL (3) | control | 3.8 | 2.1 | 5.0 | 2.9 |
| | P27 | 40.9 | 17.5 | 23.7 | 23.2 |

(1)% RR in this column is derived from proliferative responses at 50 µg/ml of peptides.
(2) not determined
(3) incorporation of /³H/thymidine (cpm × 10⁻³).

What is claimed is:
1. A hybrid molecule of
   (a) at least one peptide having a B epitope of env glycoprotein, which is a major neutralization epitope, of a virus selected from the group consisting of human immunodeficiency virus type 1 (HIV-1), human immunodeficiency virus type 2 (HIV-2), simian immunodeficiency virus (SIV), human T-cell lymphotropic virus 1 (HTLVI), and human T-cell lymphotropic virus type II (HTLV-II), wherein said peptide has at least one sequence selected from the group consisting of:
   (1) NTRKR IRIQRGPGRA FVTIGK-IGN;
   (2) NTRKK IRIQRGPGRA FVTIGK-IGN;
   (3) NTRGS IRIQRGPGRA FVTIGK-IGN;
   (4) NTRKS IYI--GPGRA FHTTGRIIGD;
   (5) NVRRS LSI--GPGRA FRTRE-IIGI;
   (6) NTRRG IHF--GPGQA LYTTGIV-GD;
   (7) NTRQR TPI--GLGQS LYTTRSR-SI;
   (8) NTRKS ITK--GPGRV IYATGQIIGD;
   (9) NTRKR ITM--GPGRV YYTTGQIIGD;
   (10) DKRQS TPI--GLGQA LYTTRGRTKI;
   (11) DKKR QSIRIGPGKV FYAKGG---I;
   (12) NTKKG IAI--GPGRT LYAREKIIGD;
   (13) HTRKR VTL--GPGRV WYTTGEILGN;
   (14) NTRRG SHF--GPGQA LYTTGIVGDI;
   (15) KITSRQQTPI--GLQA LYTTRIKGDI;
   (16) NVRRR HIHI-GPGRA FYTGEIRNI;
   (17) NTRQS TPI--GLGQA LYTTRTKSI;
   (8) NTTRS IHI--GPGRA FYATGDIIGTI;
   (19) NKRKR IHI--GPGRA FYTTKNIIGDI;
   (20) TRPNNNTRKR IRIQRGPGRA FVTIGK-IGN M-RQAH;
   (21) TRPNN TRKS IRIQRGPGRA FVTIGK-IGN M-RQAH;
   (22) TRPNNNTRKK IRIQRGPGRA FVTIGK-IGN M-RQAH;
   (23) TRPNNNTRGS IRIQRGPGRA FVTIGK-IGN M-RQAH;
   (24) TRPNNNTRKS IYI-GPGRA FHTTGRIIGD -IRKAH;
   (25) TRPYNNVRRS LSI--GPGRA FRTRE-IIGI IRQAH;
   (26) TRPGNNTRRG IHF--GPGQA LYTTGIV-GD -IRRAY;
   (27) ARPYQNTRQR TPI--GLGQS LYTTRSR-SI -IGQAH;
   (28) TRPNNNTRKS ITK-GPGRV IYATGQIIGD -IRKAH;
   (29) TRPNNNTRKR ITM--GPGRV YYTTGQIIGD -IRRAH;
   (30) TRPGSDKRQS TPI--GLGQA LYTTRGRTKI -IGQAH;
   (31) TRPGSDKKIT QSIRIGPGKV FYAKGG---I -TGQAH; and
   (32) TRPNNNTKKG IAI--GPGRT LYAREKIIGD -IRQAH; and
(b) at least one peptide having a T epitope, wherein said peptide has at least one sequence of nef protein of HIV-1 BRU selected from the group consisting of:
   (1) GMDDP EREVL EWRFD SRLAF HHVAR ELHPE YFKNC;
   (2) CYKLV PVEPD KVEEA NKGEN TSLLH PVSLH GMDDP;
   (3) EREVL EWRFD SRLAF HHVAR ELHPE YFKNC;
   (4) DSRLA FHHVA RELHP EYFKN C;
   (5) CGYFP DWQNY TPGPG VRYPL TFGWC YKLVP VEPDK;
   (6) VEEAN KGENT SLLHP V; and
   (7) CKGGL EGLIH SQRRQ DILDL WIYHT QGYFP D.

2. The hybrid molecule according to claim 1, wherein said hybrid molecule further has at least one B epitope corresponding to minor neutralization epitope of env of a virus selected from the group consisting of HIV-1, HIV-2, SIV, HTLVI, and HTLVII, and
said minor neutralization epitope has a sequence selected from the group consisting of:
(1) YDRPEGIEEEGGERDRDRSG;
(2) VAPTKAKRRVVQREKRAVGIGALFLGFL-GAG; and
(3) STQLLLNGSLAEEEVVIRC.

3. The hybrid molecule according to claim 1, wherein said molecule further has at least one T epitope, wherein said T epitope is
(1) from a protein of the same virus selected in (a), wherein said protein is not env glycoprotein; or
(2) from env glycoprotein of a HIV-1, HIV-2, SIV, HTLVI, or HTLVII.

4. The hybrid molecule according to claim 3, wherein said T epitope is encoded by a protein selected from the group consisting of p55, p25, p18, and p12 of gag of HIV-1.

5. The hybrid molecule according to claim 3, wherein said T epitope is derived from a protein from HIV-2 or SIV, and said protein corresponds to a gag protein of HIV-1 selected from the group consisting of p55, p25, p18, and p12.

6. The hybrid molecule according to any one of claims 1, 2, 3, 4, or 5, wherein said hybrid molecule further has a carrier molecule, wherein the peptide comprising a B epitope and the peptide comprising a T epitope are coupled to the carrier molecule, and said carrier molecule is selected from the group consisting of tetanus toxoid, hepatitis B surface antigen, hepatitis B core antigen, hemocyanin (KLH), and human albumin (HSA).

7. A nucleotide sequence encoding an amino acid sequence for a B epitope, which is a major neutralization epitope, of env glycoprotein of a virus selected from the group consisting of a human immunodeficiency virus type 1 (HIV-1), human immunodeficiency virus type 2 (HIV-2), simian immunodeficiency virus (SIV), human T-cell lymphotropic virus type 1 (HTLV-I), and human T-cell lymphotropic virus type II (HTLV-II), wherein said B epitope is selected from the group consisting of:
(1) NTRKR IRIQRGPGRA FVTIGK-IGN;
(2) NTRKK IRIQRGPGRA FVTIGK-IGN;
(3) NTRGS IRIQRGPGRA FVTIGK-IGN;
(4) NTRKS IYI--GPGRA FHTTGRIIGD;
(5) NVRRS LSI--GPGRA FRTRE-IIGI;
(6) NTRRG IHF--GPGQA LYTTGIV-GD;
(7) NTRQR TPI--GLGQS LYTTRSR-SI;
(8) NTRKS ITK--GPGRV IYATGQIIGD;
(9) NTRKR ITM--GPGRV YYTTGQIIGD;
(10) DKRQS TPI--GLGQA LYTTRGRTKI;
(11) DKKIR QSIRIGPGKV FYAKGG---I;
(12) NTKKG IAI--GPGRT LYAREKIIGD;
(13) HTRKR VTL--GPGRV WYTTGEILGN;
(14) NTRRG SHF--GPGQA LYTTGIVGDI;
(15) KITSRQQTPI--GLQA LYTTRIKGDI;
(16) NVRRR HIHI-GPGRA FYTGEIRNI;
(17) NTRQS TPI--GLGQA LYTTRTKSI;
(18) NTTRS IHI--GPGRA FYATGDIIGTI;
(19) NKRKR IHI--GPGRA FYTTKNIIGDI;
(20) TRPNNNTRKR IRIQRGPGRA FVTIGK-IGN M-RQAH;
(21) TRPNN TRKS IRIQRGPGRA FVTIGK-IGN M-RQAH;
(22) TRPNNNTRKK IRIQRGPGRA FVTIGK-IGN M-RQAH;
(23) TRPNNNTRGS IRIQRGPGRA FVTIGK-IGN M-RQAH;
(24) TRPNNNTRKS IYI--GPGRA FHTTGRIIGD -IRKAH;
(25) TRPYNNVRRS LSI--GPGRA FRTRE-IIGI IRQAH;
(26) TRPGNNTRRG IHF--GPGQA LYTTGIV-GD -IRRAY;
(27) ARPYQNTRQR TPI--GLGQS LYTTRSR-SI -IGQAH;
(28) TRPNNNTRKS ITK--GPGRV IYATGQIIGD -IRKAH;
(29) TRPNNNTRKR ITM--GPGRV YYTTGQIIGD -IRRAH;
(30) TRPGSDKRQS TPI--GLGQA LYTTRGRTKI -IGQAH;
(31) TRPGSDKKIT QSIRIGPGKV FYAKGG---I -TGQAH; and
(32) TRPNNNTKKG IAI--GPGRT LYAREKIIGD -IRQAH.

8. A nucleotide sequence encoding an amino acid sequence for a T epitope of nef protein of HIV-1 BRU, wherein said T epitope is selected from the group consisting of:
(1) GMDDP EREVL EWRFD SRLAF HHVAR ELKPE YFKNC;
(2) CYKLV PVEPD KVEEA NKGEN TSKKH PVSLH GMDDP;
(3) EREVL EWRFD SRLAF HHVAR ELHPE YFKNC;
(4) DSRLA FHHVA RELHP EYFKN C;
(5) CGYFP DWQNY TPGPG VRYPL TFGWC YKLVP VEPDK; and
(6) VEEAN KGENT SLLHP V.

9. An immunogenic hybrid molecule having
(a) at least one B epitope of env glycoprotein, which is a major neutralization epitope, of a virus selected from the group consisting of human immunodeficiency virus type 1 (HIV-1), human immunodeficiency virus type 2 (HIV-2), simian immunodeficiency virus (SIV), human T-cell lymphotropic virus type 1 (HTLVI), and human T-cell lymphotropic virus type II (HTLVII), said at least one B epitope is selected from the group consisting of:
(1) NTRKR IRIQRGPGRA FVTIGK-IGN;
(2) NTRKS IRIQRGPGRA FVTIGK-IGN;
(3) NTRKK IRIQRGPGRA FVTIGK-IGN;
(4) NTRGS IRIQRGPGRA FVTIGK-IGN;
(5) NTRKS IYI--GPGRA FHTTGRIIGD;
(6) NVRRS LSI--GPGRA FRTRE-IIGI;
(7) NTRRG IHF--GPGQA LYTTGIV-GD;
(8) NTRQR TPI--GLGQS LYTTRSR-SI;
(9) NTRKS ITK--GPGRV IYATGQIIGD;
(10) NTRKR ITM--GPGRV YYTTGQIIGD;
(11) DKRQS TPI--GLGQA LYTTRGRTKI;
(12) DKKIR QSIRIGPGKV FYAKGG---I;
(13) NTKKG IAI--GPGRT LYAREKIIGD;
(14) HTRKR VTL--GPGRV WYTTGEILGN;
(15) NTRRG SHF--GPGQA LYTTGIVGDI;
(16) KITSRQTPI--GLQA LYTTRIKGDI;
(17) NVRRR HIHI-GPGRA FYTGEIRNI;
(18) NTRQS TPI--GLGQA LYTTRTKSI;
(19) NTTRS IHI--GPGRA FYATGDIIGTI;
(20) NKRKR IHI--GPGRA FYTTKNIIGDI;
(21) TRPNNNTRKR IRIQRGPGRA FVTIGK-IGN M-RQAH;
(22) TRPNNNTRKS IRIQRGPGRA FVTIGK-IGN M-RQAH;

(23) TRPNNNTRKK IRIQRGPGRA FVTIGK-IGN M-RQAH;
(24) TRPNNNTRGS IRIQRGPGRA FVTIGK-IGN M-RQAH;
(25) TRPNNNTRKS IYI--GPGRA FHTTGRIIGD -IRKAH;
(26) TRPYNNVRRS LSI--GPGRA FRTRE-IIGI -IRQAH;
(27) TRPGNNTRRG IHF--GPGQA LYTTGIV-GD -IRRAY;
(28) ARPYQNTRQR TPI--GLGQS LYTTRSR-SI -IGQAH;
(29) TRPNNNTRKS ITK--GPGRV IYATGQIIGD -IRKAH;
(30) TRPNNNTRKR ITM--GPGRV YYTTGQIIGD -IRRAH;
(31) TRPGSDKRQS TPI--GLGQA LYTTRGRTKI -IGQAH;
(32) TRPGSDKKIR QSIRIGPGKV FYAKGG--I -TGQAH; and
(33) TRPNNNTKKG IAI-GPGRT LYAREKIIGD -IRQAH;

wherein said at least one B epitope is chemically coupled to (b) at least one T epitope of nef protein of BIV-1 BRU selected from the group consisting of:
(1) GMDDP EREVL EWRFD SRLAF HHVAR ELHPE YFKNC;
(2) CYKLV PVEPD KVEEA NKGEN TSLLH PVSLH GMDDP;
(3) EREVL EWRFD SRLAF HHVAR ELBPE YFKNC;
(4) DSRLA FHHVA RELHP EYFKN C;
(5) CGYFP DWQNY TPGPG VRYPL TFGWC YKLVP VEPDK;
(6) VEEAN KGENT SLLHP V; and
(7) CKGGL EGLIH SQRRQ DILDL WIYHT QGYFP D;

wherein said immunogenic hybrid molecule induces in vivo production of antibodies against said virus.

10. The hybrid molecule according to claim 9, which further comprises a carrier, wherein the B epitope and the T epitope are incorporated into the carrier, and said carrier is selected from the group consisting of tetanus toxoid, hepatitis B surface antigen, hepatitis B core antigen, hemocyanin (KLH), and human albumin (HSA).

11. The hybrid molecule according to claim 9, wherein said chemical coupling is covalent coupling.

12. The hybrid molecule according to claim 9, wherein the B epitope and T epitope are conjugated with a bridging agent to form a bridging group between the B epitope and T epitope, wherein said bridging group in the final conjugate does not exceed a chain length of 10 carbon atoms.

13. An immunogenic composition comprising a hybrid molecule of
(a) at least one peptide comprising a B epitope of env glycoprotein, which is a major neutralization epitope, of a virus selected from the group consisting of human immunodeficiency virus type 1 (HIV-1), human immunodeficiency virus type 2 (HIV-2), simian immunodeficiency virus (SIV), human T-cell lymphotropic virus type 1 (HTLVI), and human T-cell lymphotropic virus type II (HTLV-II), wherein said peptide comprises at least one sequence selected from the group consisting of:
(1) NTRKR IRIQRGPGRA FVTIGK-IGN;
(2) NTRKK IRIQRGPGRA FVTIGK-IGN;
(3) NTRGS IRIQRGPGRA FVTIGK-IGN;
(4) NTRKS IYI--GPGRA FHTTGRIIGD;
(5) NVRRS LSI--GPGRA FRTRE-IIGI;
(6) NTRRG IHF--GPGQA LYTTGIV-GD;
(7) NTRQR TPI--GLGQS LYTTRSR-SI;
(8) NTRKS ITK--GPGRV IYATGQIIGD;
(9) NTRKR ITM--GPGRV YYTTGQIIGD;
(10) DKRQS TPI--GLGQA LYTTRGRTKI;
(11) DKKIR QSIRIGPGKV FYAKGG---I;
(12) NTKKG IAI--GPGRT LYAREKIIGD;
(13) HTRKR VTL--GPGRV WYTTGEILGN;
(14) NTRRG SHF--GPGQA LYTTGIVGDI;
(15) KITSRQQTPI--GLQA LYTTRIKGDI;
(16) NVRRR HIHI-GPGRA FYTGEIRNI;
(17) NTRQS TPI--GLGQA LYTTRTKSI;
(18) NTTRS IHI--GPGRA FYATGDIIGTI;
(19) NKRKR IHI--GPGRA FYTTKNIIGDI;
(20) TRPNNNTRKR IRIQRGPGRA FVTIGK-IGN M-RQAH;
(21) TRPNN TRKS IRIQRGPGRA FVTIGK-IGN M-RQAH;
(22) TRPNNNTRKK IRIQRGPGRA FVTIGK-IGN M-RQAH;
(23) TRPNNNTRGS IRIQRGPGRA FVTIGK-IGN M-RQAH;
(24) TRPNNNTRKS IYI--GPGRA FHTTGRIIGD -IRKAH;
(25) TRPYNNVRRS LSI--GPGRA FRTRE-IIGI IRQAH;
(26) TRPGNNTRRG IHF--GPGQA LYTTGIV-GD -IRRAY;
(27) ARPYQNTRQR TPI--GLGQS LYTTRSR-SI -IGQAH;
(28) TRPNNNTRKS ITK--GPGRV IYATGQIIGD -IRKAH;
(29) TRPNNNTRKR ITM--GPGRV YYTTGQIIGD -IRRAH;
(30) TRPGSDKRQS TPI--GLGQA LYTTRGRTKI -IGQAH;
(31) TRPGSDKKIT QSIRIGPGKV FYAKGG---I -TGQAH; and
(32) TRPNNNTKKG IAI--GPGRT LYAREKIIGD -IRQAH; and (b) at least one peptide comprising a T epitope, wherein said peptide comprises at least one sequence of nef protein of HIV-1 BRU selected from the group consisting of:
(1) GMDDP EREVL EWRFD SRLAF HHVAR ELHPE YFKNC;
(2) CYKLV PVEPD KVEEA NKGEN TSLLH PVSLH GMDDP;
(3) EREVL EWRFD SRLAF HHVAR ELHPE YFKNC;
(4) DSRLA FHHVA RELHP EYFKN C;
(5) CGYFP DWQNY TPGPG VRYPL TFGWC YKLVP VEPDK;
(6) VEEAN KGENT SLLHP V; and
(7) CKGGL EGLIH SQRRQ DILDL WIYHT QGYFP D.

14. The immunogenic composition according to claim 13, wherein said hybrid molecule further comprises at least one B epitope corresponding to minor neutralization epitope of env of a virus selected from the group consisting of HIV-1, HIV-2, SIV, HTLVI, and HTLVII, and said minor neutralization epitope has a sequence selected from the group consisting of:
(1) YDRPEGIEEEGGERDRDRSG;

(2) VAPTKAKRRVVQREKRAVGIGALFLGFL-GAG; and (3) STQLLLNGSLAEEEVVIRC; and a pharmaceutically acceptable carrier.

15. The immunogenic composition according to claim 13, wherein said hybrid molecule further comprises at least one T epitope, wherein said T epitope is
   (1) from a protein of the same virus selected in (a), wherein said protein is not env glycoprotein; or
   (2) from env glycoprotein of a HIV-1, HIV-2, SIV, HTLVI, or HTLVII.

16. The immunogenic composition according to claim 15, wherein said T epitope is encoded by a protein selected from the group consisting of p55, p25, p18, and p12 of gag of HIV-1.

17. The immunogenic composition according to claim 15, wherein said T epitope is derived from a protein from HIV-2 or SIV, and said protein corresponds to a gag protein of HIV-1 selected from the group consisting of p55, p25, p18, and p12.

18. The immunogenic composition according to any one of claims 13 to 17, wherein said hybrid molecule further comprises a carrier molecule, wherein the peptide comprising a B epitope and the peptide comprising a T epitope are coupled to the carrier molecule, and said carrier molecule is selected from the group consisting of tetanus toxoid, hepatitis B surface antigen, hepatitis B core antigen, hemocyanin (KLH), and human albumin (HSA).

19. A method of inducing an immunogenic response comprising administering to a patient the immunogenic composition of claim 13.

20. A method of preparing a hybrid molecule comprising
   coupling at least one peptide comprising a B epitope of env glycoprotein, which is a major neutralization epitope, of a virus selected from the group consisting of human immunodeficiency virus type 1 (HIV-1), human immunodeficiency virus type 2 (HIV-2), simian immunodeficiency virus (SIV), human T-cell lymphotropic virus type 1 (HTLVI), and human T-cell lymphotropic virus type II (HTLV-II), wherein said peptide comprises at least one sequence selected from the group consisting of:
   (1) NTRKR IRIQRGPGRA FVTIGK-IGN;
   (2) NTRKK IRIQRGPGRA FVTIGK-IGN;
   (3) NTRGS IRIQRGPGRA FVTIGK-IGN;
   (4) NTRKS IYI--GPGRA FHTTGRIIGD;
   (5) NVRRS LSI--GPGRA FRTRE-IIGI;
   (6) NTRRG IHF--GPGQA LYTTGIV-GD;
   (7) NTRQR TPI--GLGQS LYTTRSR-SI;
   (8) NTRKS ITK--GPGRV IYATGQIIGD;
   (9) NTRKR ITM--GPGRV YYTTGQIIGD;
   (10) DKRQS TPI--GLGQA LYTTRGRTKI;
   (11) DKKIR QSIRIGPGKV FYAKGG---I;
   (12) NTKKG IAI--GPGRT LYAREKIIGD;
   (13) HTRKR VTL--GPGRV WYTTGEILGN;
   (14) NTRRG SHF--GPGQA LYTTGIVGDI;
   (15) KITSRQQTPI--GLQA LYTTRIKGDI;
   (16) NVRRR HIHI-GPGRA FYTGEIRNI;
   (17) NTRQS TPI--GLGQA LYTTRTKSI;
   (18) NTTRS IHI--GPGRA FYATGDIIGTI;
   (19) NKRKR IHI--GPGRA FYTTKNIIGDI;
   (20) TRPNNNTRKR IRIQRGPGRA FVTIGK-IGN M-RQAH;
   (21) TRPNN TRKS IRIQRGPGRA FVTIGK-IGN M-RQAH;
   (22) TRPNNNTRKK IRIQRGPGRA FVTIGK-IGN M-RQAH;
   (23) TRPNNNTRGS IRIQRGPGRA FVTIGK-IGN M-RQAH;
   (24) TRPNNNTRKS IYI--GPGRA FHTTGRIIGD -IRKAH;
   (25) TRPYNNVRRS LSI--GPGRA FRTRE-IIGI IRQAH;
   (26) TRPGNNTRRG IHF--GPGQA LYTTGIV-GD -IRRAY;
   (27) ARPYQNTRQR TPI--GLGQS LYTTRSR-SI -IGQAH;
   (28) TRPNNNTRKS ITK--GPGRV IYATGQIIGD -IRKAH;
   (29) TRPNNNTRKR ITM--GPGRV YYTTGQIIGD -IRRAH;
   (30) TRPGSDKRQS TPI--GLGQA LYTTRGRTKI -IGQAH;
   (31) TRPGSDKKIT QSIRIGPGKV FYAKGG---I -TGQAH; and
   (32) TRPNNNTKKG IAI--GPGRT LYAREKIIGD -IRQAH;

with at least one peptide comprising a T epitope, wherein said peptide comprises at least one sequence of nef protein of HIV-1 BRU selected from the group consisting of:
   (1) GMDDP EREVL EWRFD SRLAF HHVAR ELHPE YFKNC;
   (2) CYKLV PVEPD KVEEA NKGEN TSLLH PVSLH GMDDP;
   (3) EREVL EWRFD SRLAF HHVAR ELHPE YFKNC;
   (4) DSRLA FHHVA RELHP EYFKN C;
   (5) CGYFP DWQNY TPGPG VRYPL TFGWC YKLVP VEPDK;
   (6) VEEAN KGENT SLLHP V; and
   (7) CKGGL EGLIH SQRRQ DILDL WIYHT QGYFP D.

21. A method of preparing a hybrid molecule comprising the steps of transforming a host cell with a nucleotide sequence coding for a hybrid molecule of
   (a) at least one peptide comprising a B epitope of env glycoprotein, which is a major neutralization epitope, of a virus selected from the group consisting of human immunodeficiency virus type 1 (HIV-1), human immunodeficiency virus type 2 (HIV-2), simian immunodeficiency virus (SIV), human T-cell lymphotropic virus type 1 (HTLVI), and human T-cell lymphotropic virus type II (HTLV-II), wherein said peptide comprises at least one sequence selected from the group consisting of:
   (1) NTRKR IRIQRGPGRA FVTIGK-IGN;
   (2) NTRKK IRIQRGPGRA FVTIGK-IGN;
   (3) NTRGS IRIQRGPGRA FVTIGK-IGN;
   (4) NTRKS IYI--GPGRA FHTTGRIIGD;
   (5) NVRRS LSI--GPGRA FRTRE-IIGI;
   (6) NTRRG IHF--GPGQA LYTTGIV-GD;
   (7) NTRQR TPI--GLGQS LYTTRSR-SI;
   (8) NTRKS ITK--GPGRV IYATGQIIGD;
   (9) NTRKR ITM--GPGRV YYTTGQIIGD;
   (10) DKRQS TPI--GLGQA LYTTRGRTKI;
   (11) DKKIR QSIRIGPGKV FYAKGG---I;
   (12) NTKKG IAI--GPGRT LYAREKIIGD;
   (13) HTRKR VTL--GPGRV WYTTGEILGN;
   (14) NTRRG SHF--GPGQA LYTTGIVGDI;
   (15) KITSRQQTPI--GLQA LYTTRIKGDI;
   (16) NVRRR HIHI-GPGRA FYTGEIRNI;
   (17) NTRQS TPI--GLGQA LYTTRTKSI;
   (18) NTTRS IHI--GPGRA FYATGDIIGTI;

(19) NKRKR IHI--GPGRA FYTTKNIIGDI;
(20) TRPNNNTRKR IRIQRGPGRA FVTIGK-IGN M-RQAH;
(21) TRPNN TRKS IRIQRGPGRA FVTIGK-IGN M-RQAH;
(22) TRPNNNTRKK IRIQRGPGRA FVTIGK-IGN M-RQAH;
(23) TRPNNNTRGS IRIQRGPGRA FVTIGK-IGN M-RQAH;
(24) TRPNNNTRKS IYI--GPGRA FHTTGRIIGD -IRKAH;
(25) TRPYNNVRRS LSI--GPGRA FRTRE-IIGI IRQAH;
(26) TRPGNNTRRG IHF--GPGQA LYTTGIV-GD -IRRAY;
(27) ARPYQNTRQR TPI--GLGQS LYTTRSR-SI -IGQAH;
(28) TRPNNNTRKS ITK--GPGRV IYATGQIIGD -IRKAH;
(29) TRPNNNTRKR ITM--GPGRV YYTTGQIIGD -IRRAH;
(30) TRPGSDKRQS TPI--GLGQA LYTTRGRTKI -IGQAH;
(31) TRPGSDKKIT QSIRIGPGKV FYAKGG---I -TGQAH; and
(32) TRPNNNTKKG IAI--GPGRT LYAREKIIGD -IRQAH; and (b) at least one peptide comprising a T epitope, wherein said peptide comprises at least one sequence of nef protein of HIV-1 BRU selected from the group consisting of:
(1) GMDDP EREVL EWRFD SRLAF HHVAR ELHPE YFKNC;
(2) CYKLV PVEPD KVEEA NKGEN TSLLH PVSLH GMDDP;
(3) EREVL EWRFD SRLAF HHVAR ELHPE YFKNC;
(4) DSRLA FHHVA RELHP EYFKN C;
(5) CGYFP DWQNY TPGPG VRYPL TFGWC YKLVP VEPDK;
(6) VEEAN KGENT SLLHP V; and
(7) CKGGL EGLIH SQRRQ DILDL WIYHT QGYFP D;

detecting the presence of the expressed hybrid molecule; and isolating said hybrid molecule.

* * * * *

UNITED STATES PATENT AND TRADEMARK OFFICE
CERTIFICATE OF CORRECTION

PATENT NO.: 5,688,914

DATED: November 18, 1997

INVENTOR(S): Girard et al.

It is certified that an error appears in the above-identified patent and that said Letters Patent is hereby corrected as shown below:

Claim 1, col. 16, line 18, "DKKR" should read --DKKIR--.

Claim 9, col. 19, line 31, "ELBPE" should read --ELHPE--.

Signed and Sealed this

Third Day of February, 1998

Attest:

BRUCE LEHMAN

Attesting Officer

Commissioner of Patents and Trademarks